(12) United States Patent
Harding et al.

(10) Patent No.: US 8,623,280 B2
(45) Date of Patent: Jan. 7, 2014

(54) METHOD AND APPARATUS FOR MONITORING ALTERATION OF FLOW CHARACTERISTICS IN A LIQUID SAMPLE

(75) Inventors: Ian Harding, Wells (GB); Sridhar G. Iyengar, Salem, NH (US); Ha Nguyen, Quincy, MA (US); Richard Williams, Andover, MA (US)

(73) Assignee: AgaMatrix, Inc., Salem, NH (US)

( * ) Notice: Subject to any disclaimer, the term of this patent is extended or adjusted under 35 U.S.C. 154(b) by 580 days.

(21) Appl. No.: 12/947,268

(22) Filed: Nov. 16, 2010

(65) Prior Publication Data

US 2011/0083974 A1      Apr. 14, 2011

Related U.S. Application Data

(63) Continuation of application No. 11/279,044, filed on Apr. 7, 2006, now Pat. No. 7,837,941.

(51) Int. Cl.
*G01N 33/49* (2006.01)

(52) U.S. Cl.
USPC ........................... 422/73; 204/403.01; 436/69

(58) Field of Classification Search
USPC ........... 204/403.01, 400; 422/73, 68.1, 82.02; 436/69
See application file for complete search history.

(56) References Cited

U.S. PATENT DOCUMENTS

| | | |
|---|---|---|
| 3,699,437 A | 10/1972 | Ur |
| 3,967,934 A | 7/1976 | Seitz et al. |
| 4,547,735 A | 10/1985 | Kiesewetter et al. |
| 4,756,884 A | 7/1988 | Hillman et al. |
| 4,764,465 A | 8/1988 | Foung et al. |
| 4,829,011 A | 5/1989 | Gibbons |
| 4,849,340 A | 7/1989 | Oberhardt |
| 5,039,617 A | 8/1991 | McDonald et al. |
| 5,140,161 A | 8/1992 | Hillman et al. |
| 5,300,779 A | 4/1994 | Hillman et al. |
| 5,302,348 A | 4/1994 | Cusack et al. |
| 5,372,946 A | 12/1994 | Cusak et al. |
| 5,534,226 A | 7/1996 | Gavin et al. |
| 5,591,403 A | 1/1997 | Gavin et al. |
| 5,628,961 A | 5/1997 | Davis et al. |
| 6,046,051 A | 4/2000 | Jina |

(Continued)

OTHER PUBLICATIONS

Definition of term "vent", online version of Webster's Third International Dictionary, Unabridged.

(Continued)

*Primary Examiner* — J. Christopher Ball
(74) *Attorney, Agent, or Firm* — Larson & Anderson, LLC

(57) ABSTRACT

A device for measuring blood coagulation time is formed from a first substrate; a second substrate; a spacer layer disposed between the first and second substrates, said spacer layer having an opening formed therein defining a sample receiving chamber, a vented sink chamber, and an elongated reservoir forming a conduit for liquid movement between the sample receiving chamber and the sink chamber; a first electrode disposed on the first substrate, said first electrode being exposed in the reservoir portion through a first opening in the spacer layer; and a second electrode disposed on the second substrate, said second electrode being exposed in the reservoir portion through a second opening in the spacer layer. The device of the invention is used in combination with an apparatus that is connected to the first and second electrodes for measuring current flow between the first and second electrodes. Changes in observed current are indicative of flow through the device, and a cessation of flow indicates coagulation.

25 Claims, 14 Drawing Sheets

(56) References Cited

U.S. PATENT DOCUMENTS

| | | |
|---|---|---|
| 6,066,504 A | 5/2000 | Jina |
| 6,103,196 A | 8/2000 | Yassinzadeh et al. |
| 6,197,494 B1 | 3/2001 | Oberhardt |
| 6,338,821 B1 | 1/2002 | Jina |
| 6,402,704 B1 | 6/2002 | McMorrow |
| 6,451,610 B1 | 9/2002 | Gorman et al. |
| 6,620,310 B1 | 9/2003 | Ohara et al. |
| 6,673,622 B1 | 1/2004 | Jina |
| 6,750,053 B1 | 6/2004 | Widrig Opalsky et al. |
| 6,759,009 B2 | 7/2004 | Law |
| 6,830,934 B1 | 12/2004 | Harding et al. |
| 7,005,857 B2 | 2/2006 | Stiene et al. |
| 7,021,122 B1 | 4/2006 | Rosemberg et al. |
| 7,837,941 B2 * | 11/2010 | Harding et al. ........ 422/73 |
| 2004/0072357 A1 | 4/2004 | Stiene et al. |
| 2004/0073035 A1 | 4/2004 | Maase et al. |

OTHER PUBLICATIONS

Martin S. M. et al., A Microsystem for Near-Patient Accelerated Clotting Time Blood Test, Proceedings 2002, Jun. 10, 2002, pp. 1-7, vol. 39, XP001191039.

* cited by examiner

METHOD AND APPARATUS FOR MONITORING ALTERATION OF FLOW CHARACTERISTICS IN A LIQUID SAMPLE

CROSS REFERENCE TO RELATED APPLICATION

This application is a continuation application of U.S. patent application Ser. No. 11/279,044, which issued as U.S. Pat. No. 7,837,941, on Nov. 23, 2010.

BACKGROUND

The present application relates to a method and apparatus for monitoring blood coagulation or other reactions that alter flow characteristics of blood in vitro.

Monitoring of the ability of the blood to coagulate is critical to the diagnosis and treatment of several medical conditions. For patients taking anticoagulants, regular monitoring of blood coagulation is important in determining the course of treatment.

Coagulation of the blood occurs when the soluble plasma protein fibrinogen is converted into the insoluble polymer fibrin. This conversion is catalyzed by the proteolytic enzyme thrombin. Activation of thrombin is the endpoint of a cascade of activation reactions involving coagulation factors. Exposure of blood to a foreign surface initiates activation of coagulation factors forming the contact activation or intrinsic pathway, whilst damage to the blood vessel endothelium initiates activation of the tissue factor or extrinsic pathway. Several of the factors involved in promoting coagulation require modification by a Vitamin K dependent enzyme. Oral anticoagulants such as warfarin (Coumadin®) act by blocking the activation of Vitamin K to the form required during the synthesis of these coagulation factors.

The Prothrombin Time (PT) test is a standardized assay for evaluating the adequacy of coagulation by the tissue factor pathway. The tissue factor pathway can be activated in vitro by mixing blood with a preparation of thromboplastin (which comprises tissue factor and phospholipid). To perform a PT test, a standardized thromboplastin reagent is added to a blood or plasma sample, and the extent of coagulation as a function of time is monitored.

Devices are known in which the impedance of the blood sample is used as a measure of coagulation (for example, Jina U.S. Pat. No. 6,673,622). This method is used in the HemoSense® InRatio® PT test meter, which requires a small amount of blood (~15 μL), delivers a PT test result within several minutes, and is suitable for home or clinical use. However, impedance measurement of the blood sample produces a small signal, which may lead to error in determination of coagulation onset. Furthermore, impedance measurement relies on detecting a change in the electrical properties of the blood upon coagulation rather than mechanical changes in the blood. Changes in the electrical properties of coagulating blood are complex and therefore it is difficult to extract a reliable indicator of coagulation. Since coagulation is a mechanical change to the blood, making a measurement of the mechanical properties of the blood is a more direct and accurate way of determining coagulation.

Other examples of electrochemical devices for monitoring of blood coagulation are disclosed in US Patent Publication 2004/0072357, and U.S. Pat. Nos. 6,046,051, 6,066,504, 6,338,821, 6,620,310, 6,673,622, and 3,699,437.

SUMMARY OF THE INVENTION

The present invention provides a device for measuring blood coagulation time, comprising:

(a) a first substrate;
(b) a second substrate;
(c) a spacer layer disposed between the first and second substrates, said spacer layer having an opening formed therein defining a sample receiving chamber, a vented sink chamber, and an elongated reservoir forming a conduit for liquid movement between the sample receiving chamber and the sink chamber;
(d) a first electrode disposed on the first substrate, said first electrode being exposed in the reservoir portion through a first opening in the spacer layer; and
(e) a second electrode disposed on the second substrate, said second electrode being exposed in the reservoir portion through a second opening in the spacer layer.

The first and second electrodes are in electrically conductive contact with the elongated reservoir such that an electrical signal can be detected between the first and second electrodes when a conductive liquid sample is disposed in the reservoir. At least one of the electrodes is electrically insulated from the sample receiving chamber and from the sink chamber. The relative sizes of the reservoir, the sink, and a region at the connection of the reservoir and the sink are such that the time required for emptying sample from the reservoir to occur in the absence of coagulation is greater than the time required for coagulation to occur, In one embodiment, to accomplish this result, the elongated reservoir has a cross-sectional area in a plane extending perpendicular to a line extending along the elongated reservoir from the sample receiving chamber to the sink chamber, and the cross-sectional area of the elongated reservoir is smaller than parallel cross-sectional areas of the sample receiving chamber and the sink chamber. In another embodiment, a constriction is formed in the region at the connection of the reservoir and the sink. The device further includes first and second contact leads extending from the first and second electrodes, respectively, for connection of the device to an apparatus for measuring an electrochemical signal between the first and second electrodes through a sample in the reservoir.

The device of the invention is used in combination with an apparatus that is connected to the first and second electrodes for measuring current flow between the first and second electrodes. The apparatus comprises connectors configured to connect to the first and second contact leads, a signal processor for converting a current signal to an indication of coagulation time, and means for communicating the indication of coagulation time to a user.

The device of the invention is used in a method in accordance with the invention. In accordance with the method of the invention, a blood sample is introduced into the sample receiving chamber. The sample flows (passively or in response to an applied force) from the sample receiving chamber into the elongated reservoir and from there into the sink chamber. As long as a portion of the sample is present in the reservoir, current can be measured between the electrodes, However, the amount of current depends on the part of the length of the reservoir that contains sample. This means that the observed current can be related to clotting time. Thus, the final step of the method is observing the current between the electrodes and determining the clotting time from the observed current.

The determined clotting time can be used by an individual or a physician as part of a normal monitoring procedure, or it can be used in a research context as an easy way to screen candidate compounds for activity as coagulants or anti-coagulants. In addition, if the device incorporates a reagent that alters flow characteristics of the blood by agglutination or other thickening mechanism when the sample contains an analyte that interacts with the reagent to cause the change in flow characteristics, the device of the present invention can be used to assess the presence of a wide variety of analytes by observation of changes in flow characteristics as reflected in an apparent clotting time.

DETAILED DESCRIPTION OF THE INVENTION

The present invention relates to device for measuring the time it takes for coagulation or other loss of flow capability to occur in a blood or other liquid sample. In one embodiment, the measured quantity is prothrombin time of blood. However, in a more general sense, the present application uses the term "coagulation time" to refer to the time to takes for blood or other liquid sample flow through the device of the invention to stop, regardless of the specific nature of the interaction that leads to this result.

Figure 1:
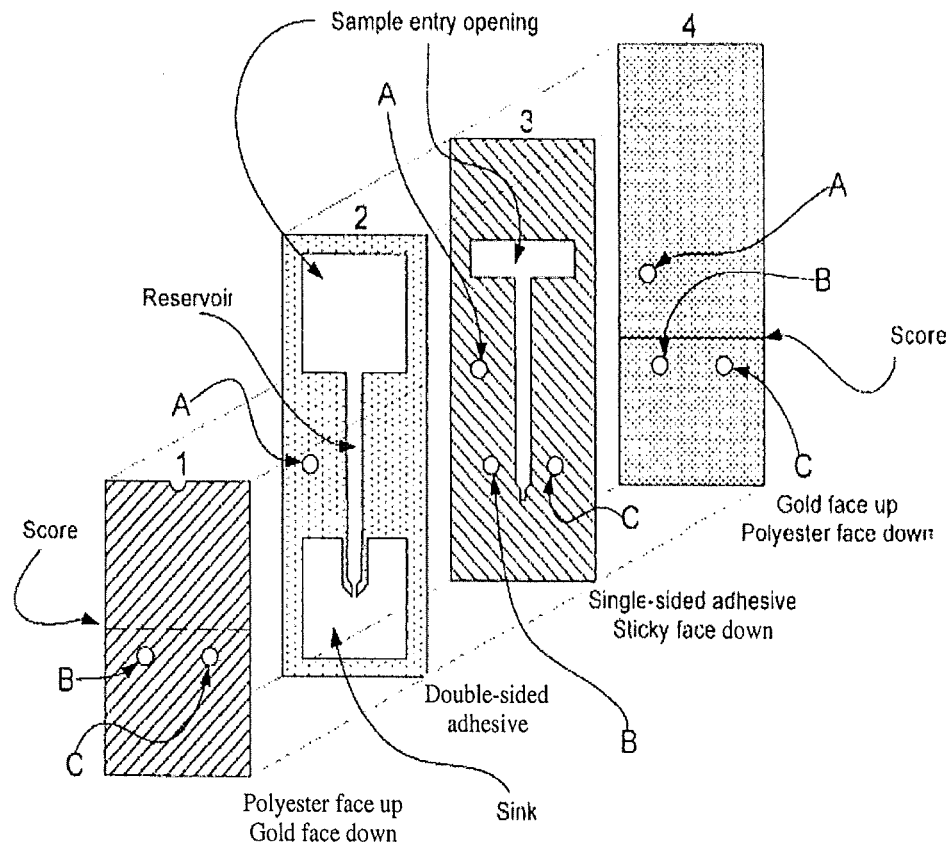
FIG. 1 shows an exploded view of a device in accordance with the invention.
Figure 2A:
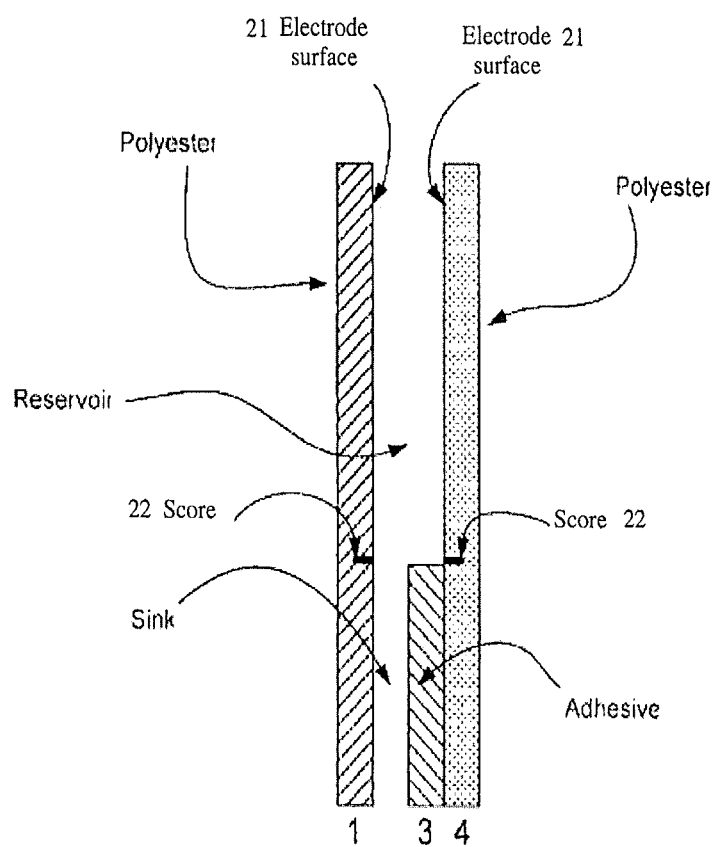
FIGS. 2A and B show a cross-sectional view through a device in accordance with the invention.

One embodiment of the device of the invention is shown in FIGS. 1 and 2A and B. As shown, the strip is formed as a sandwich of facing electrodes (e.g., gold, carbon, platinum, palladium, etc.) and adhesive layers. Layer 1 is gold on one side and polyester (insulating) on the other side. In the final test strip, the insulating polyester layer is exposed on the outer surface of the strip (face up in this diagram) and the conductive gold surface faces the interior of the strip. Layer 2 is an insulating layer with double-sided adhesive coatings. Layer 3 is an insulating layer with adhesive on one side facing layer 4. Layer 4 is gold on the side facing layer 3 and polyester (insulating) on the other side.

Cuts are formed in layers 2 and 3 to define sample entry openings and reservoir openings.

The cut in layer 2 also defines a sink opening. Therefore, the thickness of the reservoir is greater than the drain, for example twice as great if layers 2 and 3 have the same thickness. The relative thickness of the reservoir and of the sink are such that the blood flows readily into the sink by wetting action. A wetting agent (such as Triton X-100™, a non-ionic octylphenol ethoxylate surfactant of the formula alpha-[4-(1, 1,3,3-tetramethylbutyl)phenyl]-omega-hydroxypoly(oxy-1, 2-ethanediyl) or Surfactant 10-G™, which is p-nonyl phenoxypolyglycidol) may be placed in the sink to ensure that wetting drives the blood from the reservoir into the sink.

Wetting forces are influenced by many factors, including but not limited to channel dimensions, surface textures, contact angles, surface tensions, and the presence of wetting agents or wicking agents. The test strip is suitably designed to cause the wetting forces in the sink to be greater than those in the reservoir such that blood flows readily into the sink by wetting action. Thus, the reservoir may contain a surfactant as well. If this is the case, the surfactant in the sink is suitably a more effective wetting agent than the one in the reservoir, although the same surfactant may be used in both chambers, particularly if other construction factors cause a difference in the wetting action of the two chambers.

Figure 2B:
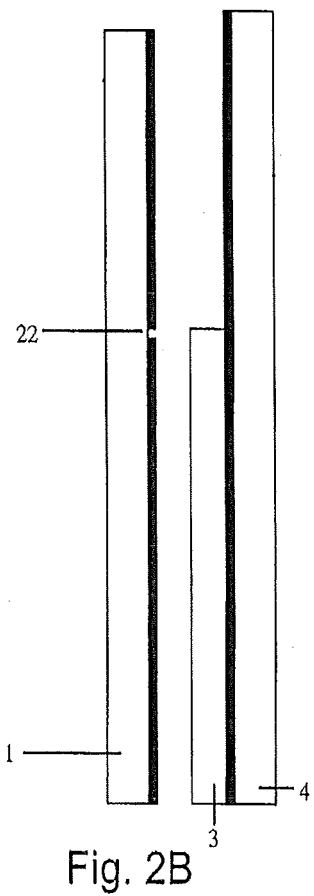

As shown in FIGS. 2A and B, the electrodes are disposed on the inner walls of the reservoir and the electrode area is defined by the openings in layers 2 and 3. Score lines 22 in layers 1, 2 and 4 can be used to define the length of the electrode surface. In principle, the electrodes may extend for the entire length of the reservoir, or may extend for only a portion of the reservoir length. The score 22 in the electrode surface of layer 1 ensures that no part of the active electrode is located in the sink. As a result, no current flows due to that portion of the sample which has left the reservoir. The layers 1 and 4 may be the same length (FIG. 2A) or of different lengths (FIG. 2B).

As the sample drains through the reservoir, a leading meniscus and a trailing meniscus may develop. A column of air will form and follow the trailing meniscus as the sample drains through. The design of the opening for delivering the sample into the reservoir will suitably facilitate the entry of air into the reservoir following the draining of the sample. For example, the opening of the reservoir may be shaped or placed in contact with certain materials such that the trailing meniscus of the sample might readily enter the reservoir.

In FIG. 1, Hole A provides an opening for electrical contact to layer 1. Holes B and C are air vents to allow for displacement of the air in the sink by sample from the reservoir.

Figure 3:
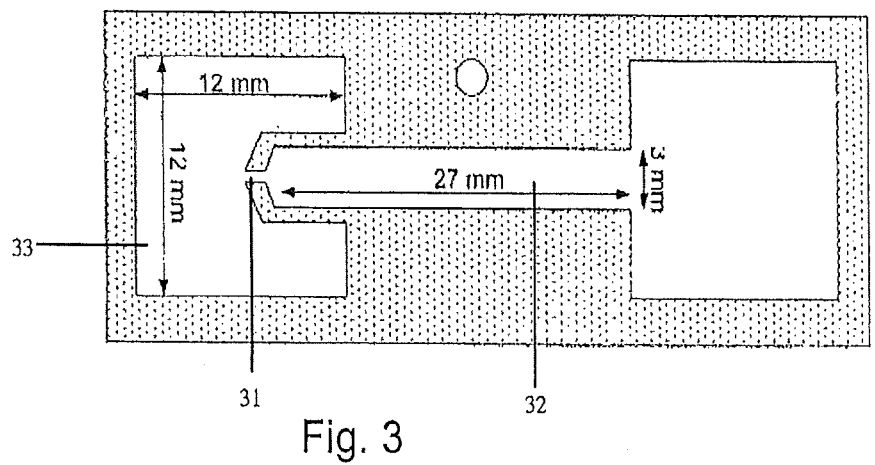
FIG. 3 shows the dimensions of the various cuts in one embodiment of layer 2 as depicted in FIG. 1.

FIG. 3 shows the dimensions of the various cuts in one embodiment of layer 2 as depicted in FIG. 1. The specific dimensions as shown are not critical, however, and may be varied. For example, the size and shape of the constriction 31 between the reservoir 32 and the sink 33 may be varied to affect the rate of flow of the sample from the reservoir to the sink. Furthermore, the overall size of each component may be changed, consistent with the overall size of the device and the intended sample volume, provided that the length and volume of the reservoir is such that meaningful current measurements can be made that distinguish between flowing and coagulated blood. This means that the relative sizes of the reservoir, the sink, and a region at the connection of the reservoir and the sink are such that the time required for emptying sample from the reservoir to occur in the absence of coagulation is greater than the time required for coagulation to occur. For example, the time required for emptying may suitably be at least 1.5 times the amount of time required for coagulation to occur in a slow-coagulating sample.

Figure 4:
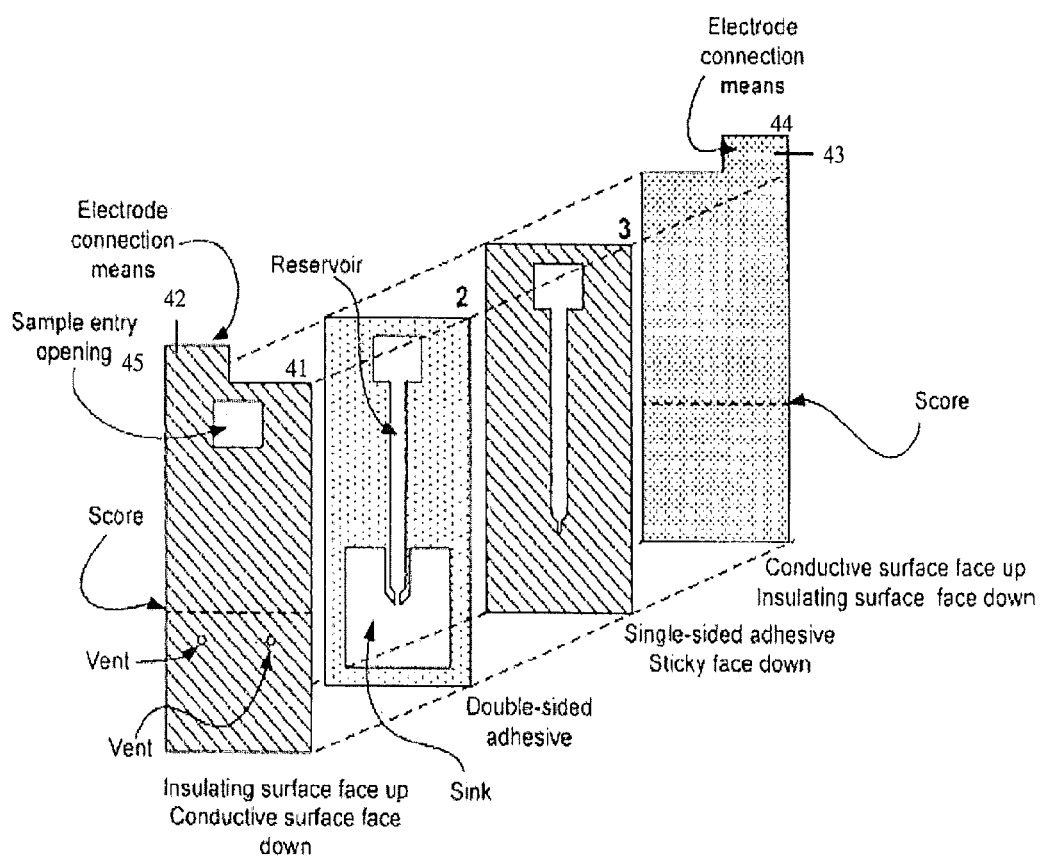
FIG. 4 shows a further embodiment of a device in accordance with the invention.

FIG. 4 shows a further embodiment of a device in accordance with the invention. In FIG. 1, layer 1 extends for only a portion of the length of the device and hole A is used to provide access to the electrode for an electrical connection. In the embodiment of FIG. 4, layer 41 has a sample entry opening 45 and a connection tab 42 and layer 44 has a symmetrical connector tab 43. The internal structure is substantially the same.

Figure 5:
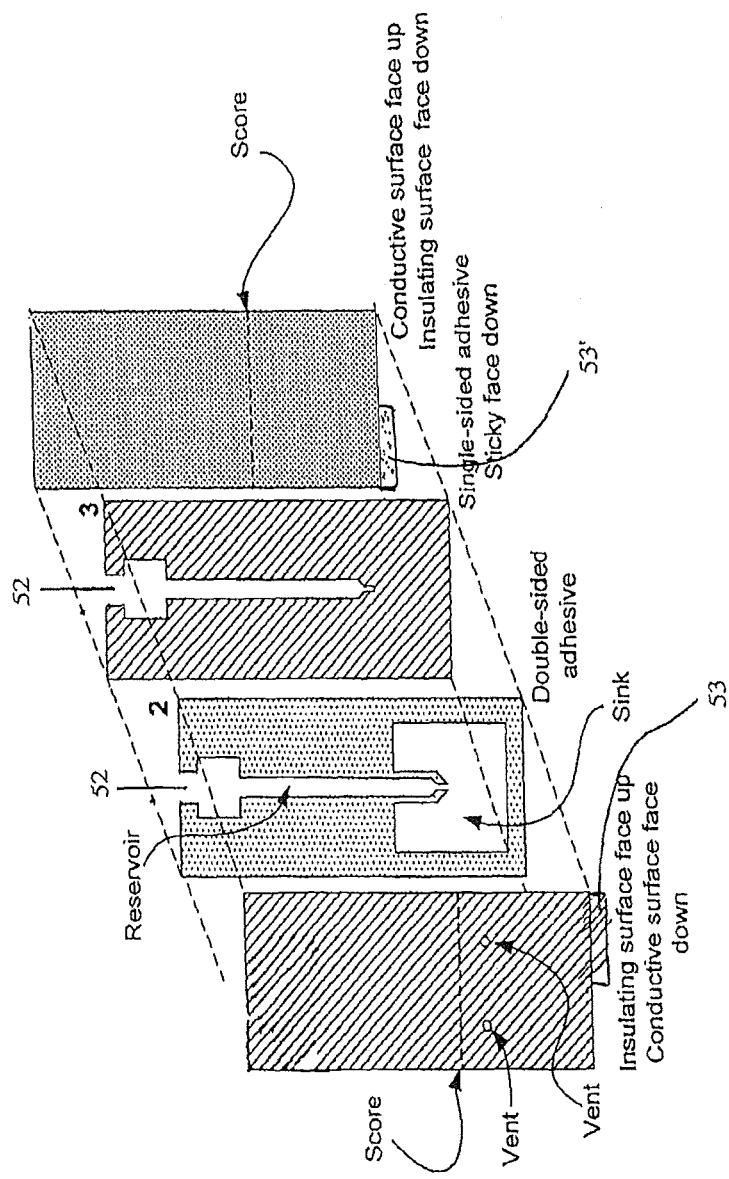
FIG. 5 shows a further embodiment of a device in accordance with the invention.

FIG. 5 shows a further embodiment of the device of the invention. In this device, the sample entry opening 52 is through the end of the device, and the connector tabs 53 and 53' extend downwards at the end opposite the sample entry opening. Modification of the score lines provides connectivity to the connector tabs 53, 53' while still electrically isolating the sink.

From these variations, it can be seen that the device of the invention generally includes:

Means for connecting the strip to a meter. Examples of such means include openings through the layers by which connection can be made to the electrode surfaces, or connector tabs extending beyond the interior insulating layers. The connector tabs can be located at either end, or on the sides of the device.

At least two electrodes in contact with the inner volume of a reservoir. The electrodes can be made from any suitable conductive material, including without limitation gold, silver, platinum, palladium, and conductive carbon. Mesh electrodes may be formed from any of these materials to increase the surface area of the electrode. In one specific embodiment, the electrodes are made from a conductive carbon mesh.

At least one opening for delivering the sample into the reservoir.

At least one opening to allow for draining of the sample from the reservoir.

At least one sink for collecting draining sample from the reservoir.

At least one air vent to allow for displacement of air in the sink by sample that collects in the sink.

In addition, the device may optionally include one or more of the following:

a reagent to promote blood coagulation that is indicative the clotting ability of the blood, which is applied during strip construction. Examples of suitable reagents include thromboplastin, reptilase, metals, such as silver (I) or mercury (II), and biopolymers such as collagen, thrombin, prothrombin, fibrin, fibrinogen, heparinase, Factor VIIa, Factor VIII, Factor IXa, Factor Xa, Factor XII, von Willebrand Factor, a selectin, a procoagulant venom, a plasminogen activator inhibitor, glycoprotein a protease, or plasma. This reagent is considered optional because it can be combined with the sample prior to introduction to the device, although this may not generally be preferred since it adds additional steps to the process. Further, in devices using a second reagent as described below, this agent may be unnecessary.

a second reagent to promote a change in flow characteristics of the blood if a target analyte material is present in the blood sample. Second reagents are suitably those that will undergo protein-protein or antibody-antigen interactions with analytes of interest that may be present in the blood. Examples of second reagents include antibodies used in blood typing, antigens to detect the presence of antibodies of interest in the blood (for example antibodies specific to disease causing organisms, and autoantibodies as in an ANA test), and antibodies to detect antigens of interest in the blood (for example prostate specific antigen (PSA) and other diagnostic cancer antigens. Stated generally, in one embodiment, the second reagent and the target analyte material are members of an antibody/antigen pair.

a reagent for modifying the surface properties of the sample (e.g., Triton X-100™ or Surfactant 10-G™), which is applied during strip construction.

a constriction between the reservoir and the sink. The constriction controls the flow rate from the reservoir so that coagulation will occur prior to complete drainage from the reservoir. The constriction is unnecessary when the dimensions of the reservoir itself are such that this characteristic is obtained.

an electron transfer agent to shuttle electrons from the electron source (e.g. the negative electrode) to the electron sink (e.g. the positive electrode). Examples of suitable electron transfer agents include, without limitation:

Ferrocenes and other metallocenes in general, with various derivatizations (expecially sulfonation).

Metal compounds and complexes (especially, but not limited to, Ru, Os, Fe, and Co) containing ligands of the following types: bipyridyl, phenanthroline, imidazole, thiolene/thiolate/thioether/sulfide, porphyrins, pyrrole/pyrrazole/thiazole/diazole/triazole, carboxylate, oxo, quinone, hydrates/hydroxo, aminates, acetates, thiolates, halides, thiocyanates, cyanides, aminoacetates, for example EDTA (Ethylenediaminetetraacetic acid), especially Fe(III)-EDTA, NTA (Nitrilotriacetic acid), ADA (beta-alaninediacetic acid), MGDA (methyleneglycine diacetic acid), IDS (iminodisuccinate), GLUDA (glutamate N,N'-bisdiacetic acid), EDDS (ethylenediamine disuccinic acid) DTPA (Diethylenetriaminepentaacetic acid); polyethers, for example cryptates and/or encapsulating ligands and crown ethers; polycarboxylates, for example citrates, oxalates, tartrates, succinates, malonates; phosphonates; polyamines with a varied number and identity of ligands in the chain, for example tetradentate ligands such as 2,3,2-triethylenetetramine [$NH_2CH_2CH_2NHCH_2CH_2NHCH_2CH_2NH_2$], 3,2,3,-triethylenetetramine [$NH_2CH_2CH_2CH_2NHCH_2CH_2NHCH_2CH_2CH_2NH_2$], 3,3,3,-triethylenetetramine [$NH_2CH_2CH_2CH_2NHCH_2CH_2NHCH_2CH_2CH_2NH_2$], NSSN-type ligands such as $NH_2CH_2CH_2SCH_2CH_2SCH_2CH_2NH_2$, $NH_2CH_2CH_2SCH_2CH_2SCH_2CH_2NH_2$, $NH_2CH_2CH_2SCH_2CH_2CH_2SCH_2CH_2NH_2$, $NH_2CH_2CH_2CH_2SCH_2CH_2SCH_2CH_2NH_2$, SNNS-type ligands such as $HSCH_2CH_2N(CH_3)CH_2CH_2N(CH_3)CH_2CH_2SH$, $HSCH_2CH_2N(CH_3)CH(CH_3)CH_2N(CH_3)CH_2CH_2SH$, $HSCH_2CH_2N(CH_3)CH_2CH_2CH_2N(CH_3)CH_2CH_2SH$, $HSC(CH_3)2CH_2NHCH_2CH_2NHCH_2C(CH_3)2CSH$, \and pendadentate ligands such as $NH_2CH_2CH_2SCH_2CH_2N(CH_3)CH_2CH_2SCH_2CH_2NH_2$, $NH_2CH_2CH_2SCH_2CH_2SCH_2CH_2SCH_2CH_2NH_2$. A preferred metal compound is ferricyanide.

Metal clusters (i.e. more than one metal in the compound)

a score in at least one of the electrode surfaces to ensure that no current flows when the sample enters a certain region of the strip, particularly the sink.

Figure 6:
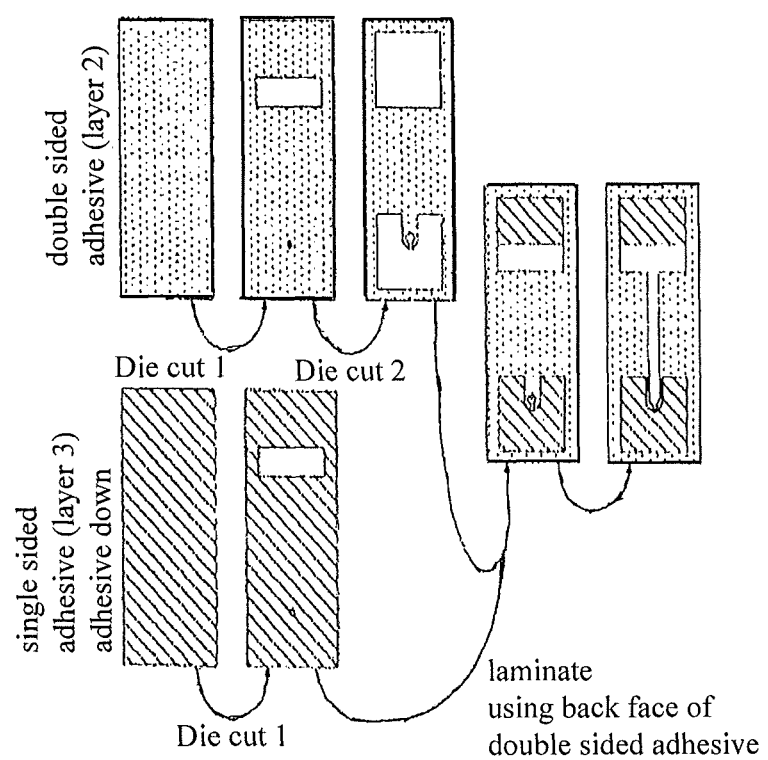
FIG. 6 shows a die cuts layers used in making a device according to the invention.

A device of the type depicted in FIGS. 2A and B can be prepared by preparing adhesive layers 2 and 3 by die cutting to form the sample openings and the sink as shown in FIG. 6. These layers are laminated together, and then a further cut is made to form the reservoir. The resulting structure is attached to the gold sides of the polyester substrate layer 4 (see FIG. 2A or B above). Excess adhesive and gold layers that may be present, and that may have been used for alignment during die cutting is removed, and hole A is punched. If desired, thromboplastin (sold under the trade name Innovin®) is applied to the reservoir and CMC Triton® X-100 is applied to the sink. After air drying, layer 1 is applied and excess gold that may be present at the bottom of layer 1 and have been used for alignment during die cutting is removed and holes B and C are punched. If multiple strips were made as a unit, they can be cut apart before or after punching of holes B and C, and this cutting may also accomplish any necessary trimming or extra materials.

Figure 7A:
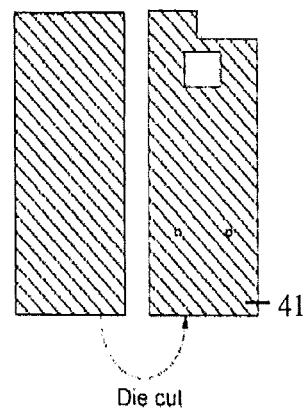
FIGS. 7A-F show construction steps in making one embodiment of the device of the invention.
Figure 7B:
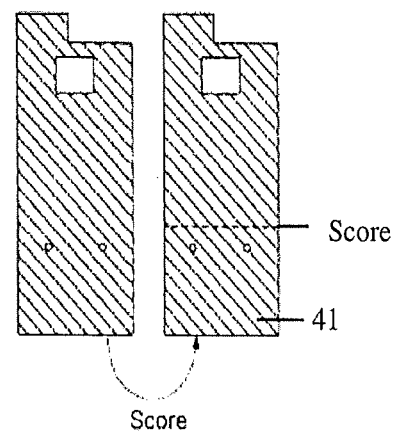

A device of the type depicted in FIG. 4 can be prepared using the steps outlined in FIG. 7A-F. As shown in FIG. 7A, layer 41 is produced from a sheet of conductive material that is insulated on one surface. A single die may be used to produce all features of this layer, except for the score on the conductive surface. The layer is then scored in the desired pattern, in this case a transverse line (FIG. 7B). In this and all other instances of scoring referenced herein, the scoring of the conductive surfaces can be accomplished by laser etching, mechanical scoring using a blade, or any other technique that results in a break in the conductive coating but not the underlying insulation.

Figure 7C:
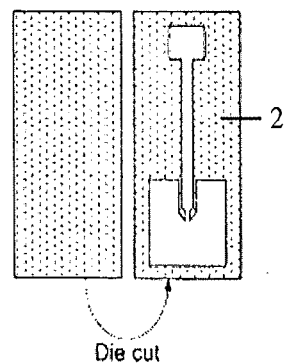

Layer 2 is an insulating spacer layer, and is suitably a double-sided adhesive layer. It will be appreciated, however, that separate adhesive layers or subsequently applied adhesive can be employed or that the layers might be joined by heat sealing in all embodiments of the invention where adhesive layers are described. All features of this layer may be produced by a single die cut as shown in FIG. 7C.

Figure 7D:
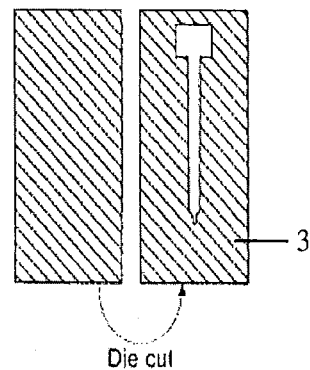

Layer 3 is a an insulating spacer layer, and is suitably a single-sided adhesive layer. All features of this layer may be produced by a single die cut as shown in FIG. 7D.

Figure 7E:
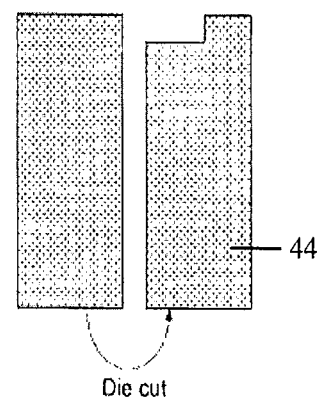
Figure 7F:
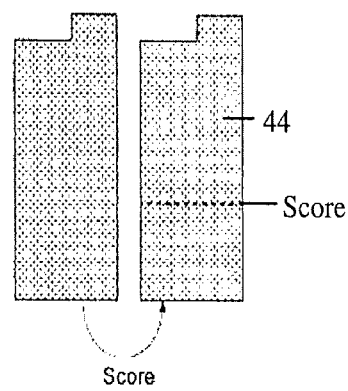

Layer 44 is produced from a sheet of conductive material that is insulated on one surface. A single die may be used to produce all features of this layer, except for the score on the conductive surface (FIG. 7E). The score, if desired, in then formed (FIG. 7F).

The layers made in accordance with FIGS. 7A-F are laminated together to complete the assembly of the device. Layer lamination, application of reagent(s) to the test strip, and drying of the strip once reagent has been applied may occur at different steps along the fabrication process.

Figure 8A:
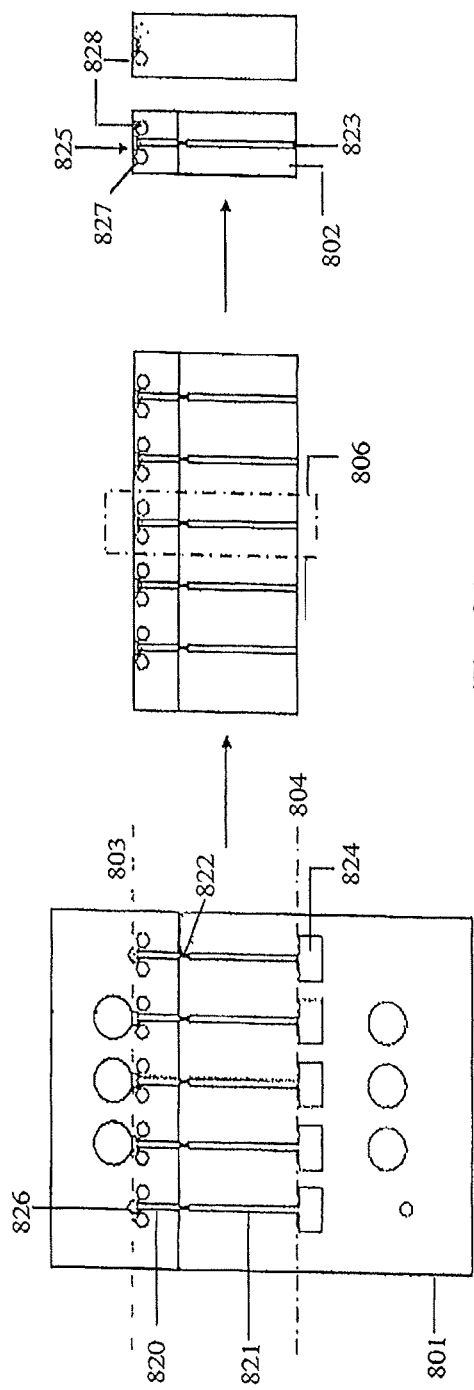
FIGS. 8A and B show the parts of one embodiment of the invention manufactured as a multi-device sheet.

If desired, the devices of the invention can be made by forming multiple devices on a single series of die-cut sheets, and then cutting the resulting composite apart to provide individual devices. FIG. 8A shows such a composite sheet 801 that can be cut apart to form five devices 802 along cut lines 803 and 804, and vertical cut lines 805 and 806.

Figure 8B:
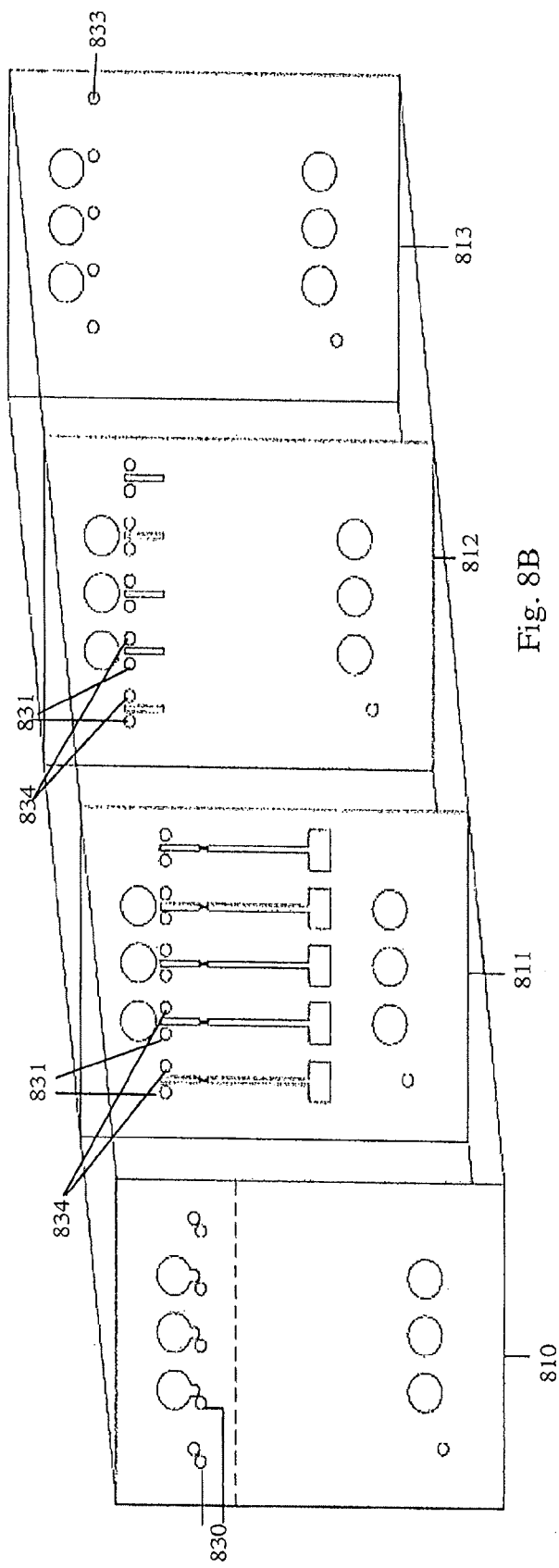

FIG. 8B shows the layers that are used to make up the composite sheet 801. Layer 810 has the electrode material, for example gold on the upper surface as shown, and a substrate material such as polyester on the other surface. Layer 811 is a spacer/insulating layer and is adhered to the electrode side of layer 810. Layer 812 is a second spacer/insulating layer that is disposed over layer 811. Layer 813 has electrode material disposed on the side facing layer 812, and a substrate such as polyester on the outside, In the devices of the FIG. 8A, each device has a reservoir 820 and a sink 821 separated by a constriction 822. The sink 821 is vented at the bottom 823 through a hole that results when the device is separated from the composite sheet 801 along cut line 804. Larger holes 824 at the end of the sink facilitate the formation of this vent hole. The sample addition opening 825 is formed the top end of the device when it is cut from the composite sheet 801 along cut line 803. Registration holes 805 can be positioned at the sample addition ends of at least some of devices to assist in the formation of the sample addition hole. Alternatively, some or all of the devices can be formed with a supplemental opening 826 adjacent to the sample addition opening on at least layers 810 and 813. Opening 826 has a shape that aids in the entry of air to the device after the sample has entered.

Holes 830 in sheet 810 are in alignment with alternating holes 831 in sheets 811 and 812, while holes 833 are in alignment with the other set of alternating holes 834 in sheets 811 and 812. As a result, electrode contacts 827 and 828 are formed on facing sides of the device 802.

The device of the invention is used in a combination comprising a test device and an apparatus or meter. In the combination of the invention, the apparatus is connected to the first and second electrodes for measuring current flow between the first and second electrodes. The apparatus comprises connectors configured to connect to the first and second contact leads, a signal processor for converting a current signal to an indication of coagulation time, and means for communicating the indication of coagulation time to a user.

Figure 9:
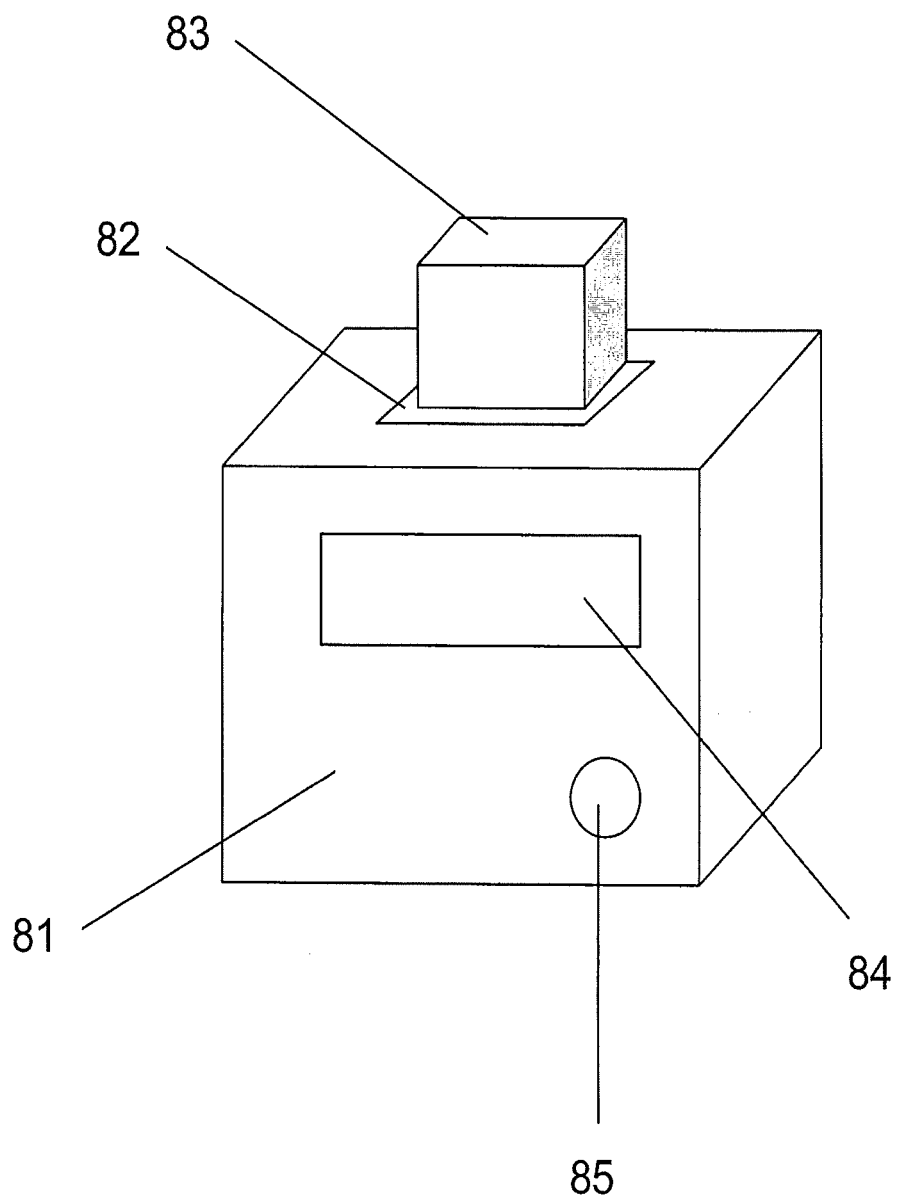
FIG. 9 shows an exterior view of a combination in accordance with the invention.

FIG. 9 shows an exterior view of a combination in accordance with the invention. As shown, the apparatus has a housing 81 with a slot 82 into which device 83 is received. When device 83 is correctly inserted into the slot 82 it makes contact with the connectors that measure current between the electrodes of the device. Display 84 provides means for communicating a qualitative or quantitative result to a user. Examples of suitable displays include LED and LCD displays. Communications may also occur through wired or wireless transmission of results to a separate device. Buttons, such as button 85 may be supplied for turning the apparatus on and off. The meter also comprises a processor with appropriate instructions sets and storage capability to determine the coagulation time and communicate it to a user.

Figure 10A:
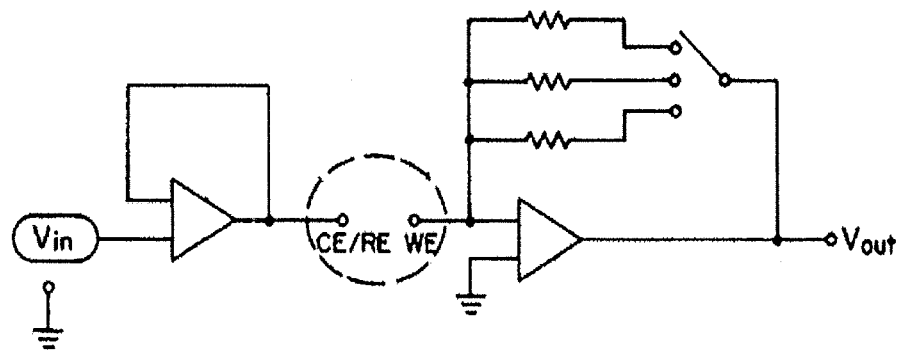
FIGS. 10A and B show circuits that can be used to evaluate the current between the electrodes.
Figure 10B:
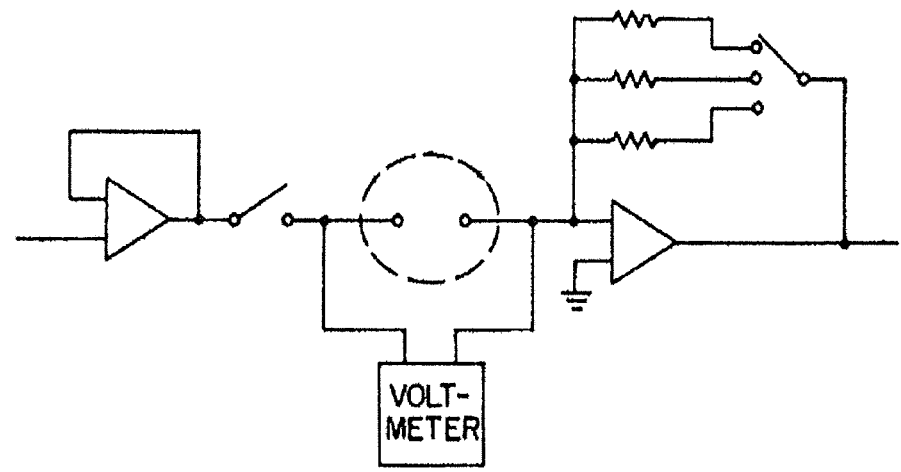

FIGS. 10A and B shows a circuit that can be used to evaluate the current between the electrodes and hence the coagulation time of the sample. FIG. 10A shows an arrangement where the counter electrode and the reference electrode can be combined into one single electrode. FIG. 10B is an improvement over the previous design; the inclusion of a voltmeter that can measure the potential across the electrodes. These circuit designs are mere examples and the invention is by no means restricted to the ones shown in the figures. The potential applied between the electrodes may be a steady state potential difference or it may be an AC potential. A wide range of frequencies may be used. Thus, in one pair of experiments using venous blood in a device coated with Triton X-100™, comparable results were observed using AC potentials with a frequency of 0.5 Hz and 100 Hz. The frequency modulation in an applied AC potential may take the shape of a sine-wave but other potential shapes, including sawtooth shapes may also be used.

Figure 11:
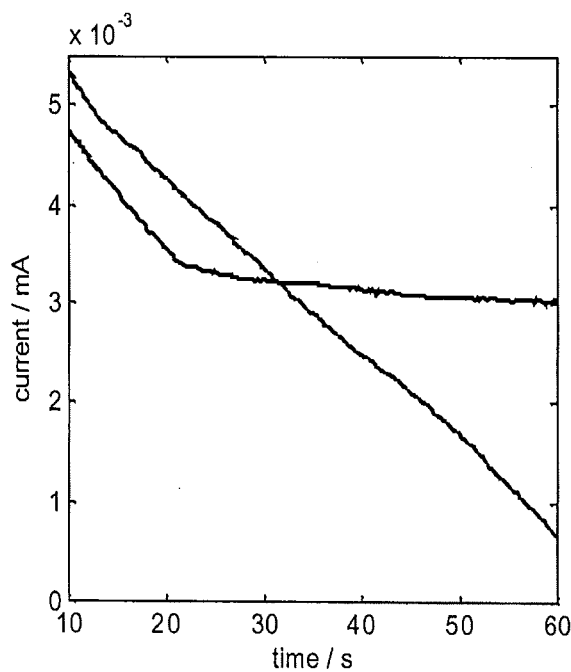
FIG. 11 shows two current profiles, one in which blood coagulates and the other in which is does not.

To use the device and combination of the present invention, the user places a test device in a test meter, and applies a small sample of blood (for example about 15 microliters) to the sample entry port on the test device. Application of blood can be detected based on resistance between the electrodes, or a manual start signal can be given, for example using button 85 in FIG. 9. Current is measured across the reservoir and between the electrodes. FIG. 11 shows two current profiles, one in which blood coagulates and the other in which is does not. The two samples both contain Innovin, which promotes coagulation. However, to the sample indicated by the dashed line EDTA is also added. EDTA sequesters $Ca^{2+}$ and prevents coagulation even in the presence of Innovin®.

As shown in FIG. 11, there is an initial steep decline in current which corresponds to the decrease in electrode area as blood drains from the reservoir into the sink in both samples, although the rate of decay is not identical. In the sample to which EDTA is not added, the decay is slower and there is a sharp transition to a fairly constant plateau current. This current profile can be used to provide an assessment of coagulation time by any of several methods.

An assessment of coagulation time can be determined from the rate of decay of the current. Rate of decay can be determined by frequency analysis, the initial slope or curve fitting and extrapolating to a time of zero, or predetermined low current. The predetermined low current may, for example, be set of an average value of plateau current which is discussed further below.

An assessment of coagulation time can also be made by determining the time at which the phase transition from flowing to coagulated occurs, as reflected by the sudden "elbow" in the current profile. This can be detected by changes in the slope. By way of non-limiting example, with reference to FIG. 12, the current profile can be seen to have two parts: a declining portion with a slope of −0.15 mA/s, and a plateau portion with a slope of −0.01 mA/s. For any given experimental configuration and units, the intermediate numerical value which characterizes the transition from one slope to the other with a suitable degree of reliability can be determined empirically. It may also be determined as the point at which the second derivative of the slope is at a maximum.

Figure 12:
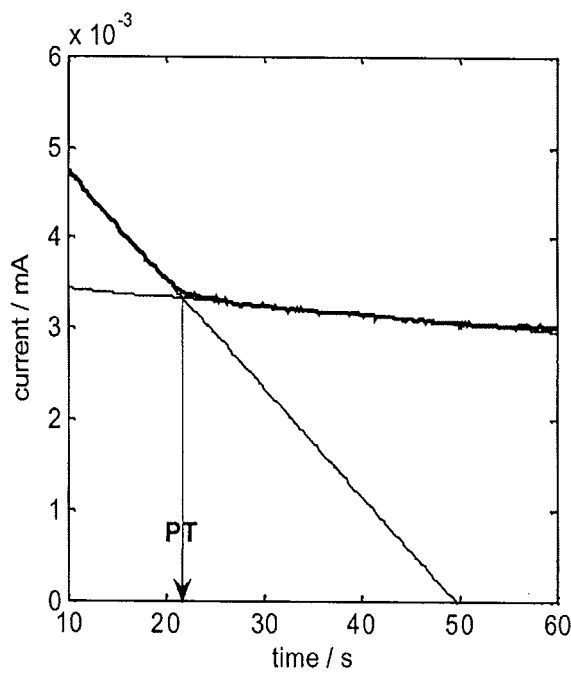
FIG. 12 schematically depicts the determination of plateau current time by extrapolation.

In a preferred embodiment, coagulation time is determined from a combination of initial slope and the plateau current as illustrated in FIG. 12. Determination of plateau current may be made when the slope of the current is within a certain limit of zero. Alternatively, a Cottrell current analysis may be used to determine if the current has reached the plateau current. Fourier analysis may also be used to determine if the current has reached the plateau current. The time at which the extrapolated initial decay passes through the value of the plateau current is taken as the value of coagulation time PT.

Coagulation time may also be determined on the basis of the value of the measured current. For example, from FIG. 11, the measured current at 60 seconds in the solid line corresponds to a certain coagulation time. Similarly, current measured at 60 seconds for an array of decay profiles (not shown in FIG. 11) will correspond to different coagulation times. Therefore, for any given apparatus and known manufacturing tolerances one can establish a calibration constant or curve that relates the measured amount of current at a time when the plateau has consistently been achieved with the coagulation time.

Figure 13:
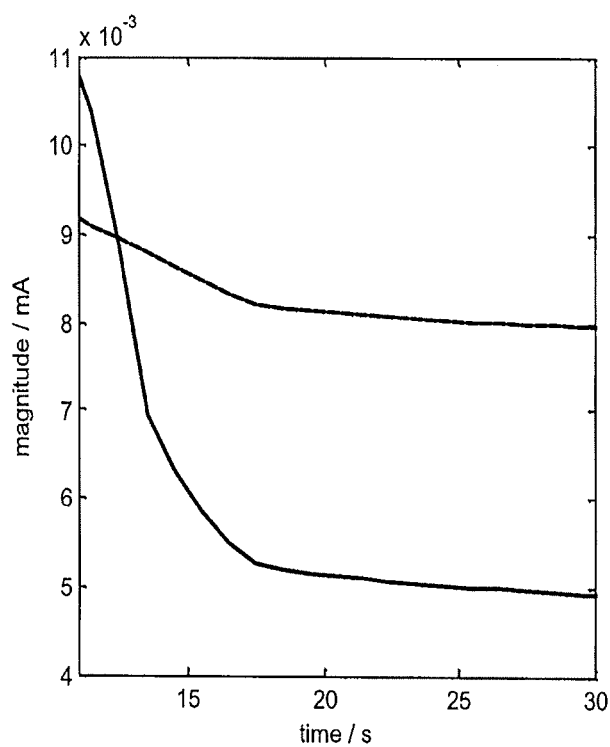
FIG. 13 shows current profiles for a device in accordance with the invention using two different wetting agents.

FIG. 13 shows current profiles for a device in accordance with the invention using two different wetting agents. As shown, the change in current is more pronounced when Surfactant 10-G™ is used (solid line) than when Triton X-100™ is used.

Figure 14:
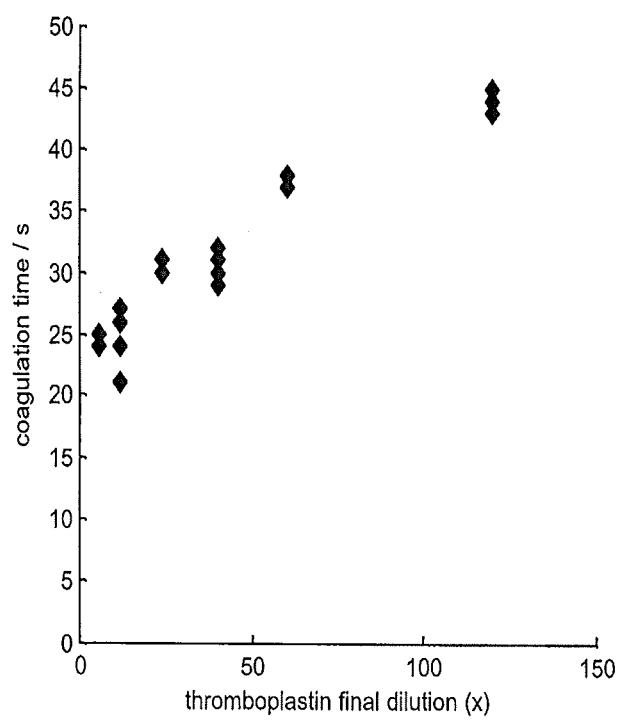
FIG. 14 shows the results from a series of experiments in which coagulation times were observed when venous blood was exposed to different amounts of thromboplastin.

FIG. 14 shows the results from a series of experiments in which coagulation times were observed when venous blood was exposed to different amounts of thromboplastin to result in different coagulation times. As shown, the expected linear relationship was observed between the measured coagulation time and the amount of thromboplastin with less thromboplastin (higher dilution) resulting in longer coagulation times.

As noted above, the device and method of the invention can also be used to detect changes in flow characteristics of a liquid sample that are the result of protein-protein interaction, antibody-antigen, antibody-hapten or other specific binding interactions. The following examples are provided to further elucidate such uses but are not intended to be limiting on the scope of the invention, In a first non-limiting example, the device of the invention is used for pathogen identification/classification to distinguish *Staphylococcus aureus* from other members of the genus such as *S. hyicus*. This application of the invention is based on the presence of clumping factor on cells *S. aureus* but not on cells of other members of the genus. Clumping factor binds to fibrinogen or fibrin present in human blood or rabbit plasma resulting in agglutination of cells and thus in a change of flow characteristics. Thus, in accordance with the present invention, a sample containing *S. aureus* can be distinguished from a staph sample of another species by introduction into of the sample into a device of the invention where the device contains fibrinogen or fibrin. The fibrinogen or fibrin may be present in the device prior to introduction of the sample, for example coated on the walls of the device, or may be added with the sample. Additional *S. aureus* specific binding materials, such as anti-protein A immunoglobulin G may be used in addition or in the alternative to fibrin or fibrinogen.

By way of a second non-limiting example, blood type can be determined using standard antibodies to A, B and Rh antigens and the addition of a whole blood sample. The antibodies specific to A, B and Rh antigens are well known, and are routinely used in blood testing. Rapid testing, however, may require the visual observation and subjective determination of agglutination as an indication of a positive test. Placing the antibody in the device of the present invention, either before or with the sample results in a numerical result rather than a subjective assessment, and therefore provide a more consistent yet still rapid determination of blood type.

By way of a third non-limiting example, tests for hemagglutinin found on the surface of influenza and other virus are commonly performed in a V-bottom microtiter plate using dilutions of attenuated viral particles and a constant concentration of red blood cells. The dilutions are used to determine the amount of virus present, but are cumbersome and require a trained technician. Adherence of the red blood cells is observed as an indication of the presence and activity of viral hemagglutinin by tilting the wells and looking for the absence of flow. This test is not only subjective, but for the most parts the titer of viral particles in biological fluids is insufficient to make this test of diagnostic relevance. Hemagglutination reactions to detect antibodies are also known based on antigen-coated reagent erythrocytes. In either case, change in flow characteristics of the type monitored in the present invention are used. Thus, the present invention can be used to detect viral hemagglutinin or on other hemagglutination reactions by introducing the sample fluid with red blood cells (native or antigen coated) or antigen-coated particles that mimic the red blood cells and observed changes in flow characteristics. Because a reduction in flow can observed as well as complete cessation, dilutions to obtain an estimate of viral titer are not required.

In the foregoing examples and drawings, the surfaces of the substrates and the electrodes are shown in a generally planar configuration. The invention is not limited to such a configuration, however. For example, the substrate and/or the electrode may have a sawtooth or undulating surface which can increase the length of the sample space/reservoir without having to increase the overall length of the device. Similarly, while the tube is depicted as generally linear, a tube in the shape of a J, inverted-J or U or other bent shapes can be used to increase the length available for sample flow as well.

The devices of the invention are also depicted utilizing passive flow, based either on gravitational flow or capillarity due to the spacing between the walls. The device of the invention may also make use of assisted flow, for example using pressure or suction.

The devices of the invention are also depicted as having a single chamber extending from the sample insertion point to the reservoir. The invention includes devices that have multiple chambers arranged in the same device, or chambers that are branched. For example, the chamber could be bifurcated or trifurcated, with multiple reservoirs connected to a common sample application point. These reservoirs may each have an individual sink, or can be connected to a common sink. A branched chamber can have different reagents, or different amounts of reagents in each branch to allow for determination of multiple distinct results. For example, separate branches of a trifurcated chamber could contain the antibodies for A, B and Rh antigens such that a single test would fully type a blood sample with respect to the most common blood types.

What is claimed is:

1. A device for measuring blood coagulation time, comprising:
   (a) a first substrate;
   (b) a second substrate;
   (c) a spacer layer disposed between the first and second substrates, said spacer layer having an opening formed therein defining a sample receiving chamber, a vented sink chamber, and an elongated reservoir forming a conduit for liquid movement between the sample receiving chamber and the sink chamber;
   (d) a first electrode disposed on the first substrate, said first electrode being exposed through the reservoir portion of the opening in the spacer layer; and
   (e) a second electrode disposed on the second substrate, said second electrode being exposed through the reservoir portion of the opening in the spacer layer;
   wherein the first and second electrodes are in electrically conductive contact with the elongated reservoir such that an electrical signal can be detected between the first and second electrodes when a conductive liquid sample is disposed in the reservoir and at least one of the electrodes is electrically insulated from the sample receiving chamber and from the sink chamber, wherein the relative sizes of the reservoir, the sink, and a region at the connection of the reservoir and the sink are such that the time required for emptying sample from the reservoir into the sink to occur in the absence of coagulation is greater than the time required for coagulation to occur; and
   (f) first and second contact leads extending from the first and second electrodes, respectively, for connection of the device to an apparatus for measuring an electrochemical signal between the first and second electrodes through a sample in the reservoir.

2. The device of claim 1, further comprising a reagent effective to promote coagulation of blood that is indicative of the clotting ability of the blood, said reagent disposed to contact a blood sample introduced to the sample receiving chamber.

3. The device of claim 2, wherein the reagent is thromboplastin.

4. The device of claim 1, wherein the first and second electrodes are formed from gold.

5. The device of claim 1, wherein the reservoir has a narrowed portion separating a main portion of the reservoir from the sink.

6. The device of claim 1, further comprising a wetting agent effective to promote flow of blood from the sample receiving chamber through the reservoir to the sink chamber.

7. The device of claim 6, wherein the wetting agent is an ocytlphenol ethoxylate or p-nonyl phenoxypolyglycidol.

8. The device of claim 1, wherein the sample receiving chamber, reservoir and sink chamber each have a width dimension and a smaller depth dimension, and wherein the depth dimension of the sink chamber is less than the depth dimension of the reservoir.

9. The device of claim 8, further comprising a reagent effective to promote coagulation of blood disposed to contact a blood sample introduced to the sample receiving chamber.

10. The device of claim 9, wherein the reagent is thromboplastin.

11. The device of claim 8, wherein the first and second electrodes are formed from gold.

12. The device of claim 8, wherein the reservoir has a narrowed portion separating a main portion of the reservoir from the sink.

13. The device of claim 8, further comprising a wetting agent effective to promote flow of blood from the sample receiving chamber through the reservoir to the sink chamber.

14. The device of claim 13, wherein the wetting agent is an ocytlphenol ethoxylate or p-nonyl phenoxypolyglycidol.

15. The device of claim 1, wherein the elongated reservoir has a cross-sectional area in a plane extending perpendicular to a line extending along the elongated reservoir from the sample receiving chamber to the sink chamber, and the cross-sectional area of the elongated reservoir is smaller than parallel cross-sectional areas of the sample receiving chamber and the sink chamber 16. The device of claim 1, further comprising a second reagent effective to promote more rapid coagulation of blood if a target analyte material is present in the blood sample, said second reagent being disposed to contact a blood sample introduced to the sample receiving chamber.

17. The device of claim 1, wherein second reagent and the target analyte material are members of an antibody/antigen pair.

18. A method for determining coagulation time of a blood sample, comprising the steps of:
   (a) introducing a blood sample into a device for measuring blood coagulation time wherein the sample is combined with a reagent effective to promote coagulation of blood disposed to contact a blood sample introduced to the sample receiving chamber in the device, said device comprising:
      a first substrate;
      a second substrate;
      a spacer layer disposed between the first and second substrates, said spacer layer having an opening formed therein defining a sample receiving chamber, a vented sink chamber, and an elongated reservoir forming a conduit for liquid movement between the sample receiving chamber and the sink chamber;
      a first electrode disposed on the first substrate, said first electrode being exposed through the reservoir portion of the opening in the spacer layer; and
      a second electrode disposed on the second substrate, said second electrode being exposed through the reservoir portion of the opening in the spacer layer,
   wherein the first and second electrodes are in electrically conductive contact with the elongated reservoir such that an electrical signal can be detected between the first and second electrodes when a conductive liquid sample is disposed in the reservoir and at least one of the electrodes is electrically insulated from the sample receiving chamber and from the sink chamber, wherein the relative sizes of the reservoir, the sink, and a region at the connection of the reservoir and the sink are such that the time required for emptying sample from the reservoir into the sink to occur in the absence of coagulation is greater than the time required for coagulation to occur,
   (b) measuring current between the first and second electrodes, and (c) determining from the change in measured current a coagulation time.

19. The method of claim 18, wherein the coagulation time is determined from the rate of decay of the current.

20. The method of claim 19, wherein the coagulation time is determined from extrapolation of the initial slope of current as a function of time to a current of zero.

21. The method of claim 19, wherein the coagulation time is determined from extrapolation of the initial slope of current as a function of time to a predetermined low current value.

22. The method of claim 21, wherein the predetermined low current value is average value of measured plateau currents for the device.

23. The method of claim 18, wherein the determination of coagulation time is made by detection of changes in slope of current as a function of time when the phase transition from flowing to coagulated occurs.

24. The method of claim 18, wherein the coagulation time is the time at which the initial slope of current as a function of time intersects the slope of the plateau current.

25. A combination comprising
(a) a device for measuring blood coagulation time, comprising:
a first substrate;
a second substrate;
a spacer layer disposed between the first and second substrates, said spacer layer having an opening formed therein defining a sample receiving chamber, a vented sink chamber, and an elongated reservoir forming a conduit for liquid movement between the sample receiving chamber and the sink chamber;
a first electrode disposed on the first substrate, said first electrode being exposed through the reservoir portion of the opening in the spacer layer; and
a second electrode disposed on the second substrate, said second electrode being exposed through the reservoir portion of the opening in the spacer layer,
wherein the first and second electrodes are in electrically conductive contact with the elongated reservoir such that an electrical signal can be detected between the first and second electrodes when a conductive liquid sample is disposed in the reservoir and at least one of the electrodes is electrically insulated from the sample receiving chamber and from the sink chamber, wherein the relative sizes of the reservoir, the sink, and a region at the connection of the reservoir and the sink are such that the time required for emptying sample from the reservoir into the sink to occur in the absence of coagulation is greater than the time required for coagulation to occur; and
first and second contact leads extending from the first and second electrodes, respectively, for connection of the device to an apparatus for measuring an electrochemical signal between the first and second electrodes through a sample in the reservoir; and
(b) an apparatus connected to the first and second electrodes for measuring current flow between the first and second electrodes, said apparatus comprising connectors configured to connect to the first and second contact leads, a signal processor for converting a current signal to an indication of coagulation time, and means for communicating the indication of coagulation time to a user.

* * * * *